United States Patent [19]

Goldberg

[11] Patent Number: 5,611,811

[45] Date of Patent: Mar. 18, 1997

[54] MICRO AND MINI HAIR TRANSPLANT DEVICE

[75] Inventor: Paul M. Goldberg, Matawan, N.J.

[73] Assignee: Star-Wood, Inc., Matawan, N.J.

[21] Appl. No.: 236,563

[22] Filed: Apr. 29, 1994

[51] Int. Cl.⁶ .................................................. A61B 17/34
[52] U.S. Cl. ........................................................ 606/187
[58] Field of Search .............................. 606/1, 133, 187; 604/57–63

[56] References Cited

U.S. PATENT DOCUMENTS

| | | |
|---|---|---|
| 3,219,022 | 11/1965 | Hagemeyer . |
| 3,774,607 | 11/1973 | Schmitz ..................................... 604/61 |
| 3,867,942 | 2/1975 | Bellantoni et al. . |
| 3,998,230 | 12/1976 | Miller . |
| 4,223,674 | 9/1980 | Fluent et al. .............................. 604/61 |
| 4,476,864 | 10/1984 | Tezel . |
| 4,751,927 | 6/1988 | Yamada . |
| 4,762,515 | 8/1988 | Grimm ...................................... 604/61 |
| 4,931,060 | 6/1990 | Aue .......................................... 606/188 |
| 5,269,801 | 12/1993 | Shiau ....................................... 606/187 |
| 5,370,611 | 12/1994 | Niezink et al. ........................... 604/62 |
| 5,417,683 | 5/1995 | Shiao ........................................ 606/1 |
| 5,439,475 | 8/1995 | Bennett .................................... 606/187 |

FOREIGN PATENT DOCUMENTS 2809327  4/1979  Germany ............................... 606/187

OTHER PUBLICATIONS

J. Dermatol Surg Oncol:Choi et al, "Single Hair Translplantation Using Choi Hair Transplanter" 1992 pp. 945–948.

Primary Examiner—Glenn Dawson
Attorney, Agent, or Firm—Arthur M. Peslak

[57] ABSTRACT

A device for automating hair transplant procedures. The device includes a part for puncturing the scalp, a part for containing the hair grafts to be transplanted, a part for ejecting the hair grafts from the containing means, a part for actutating the the ejecting means and a part for delivering the hair grafts into the transplant site.

4 Claims, 5 Drawing Sheets

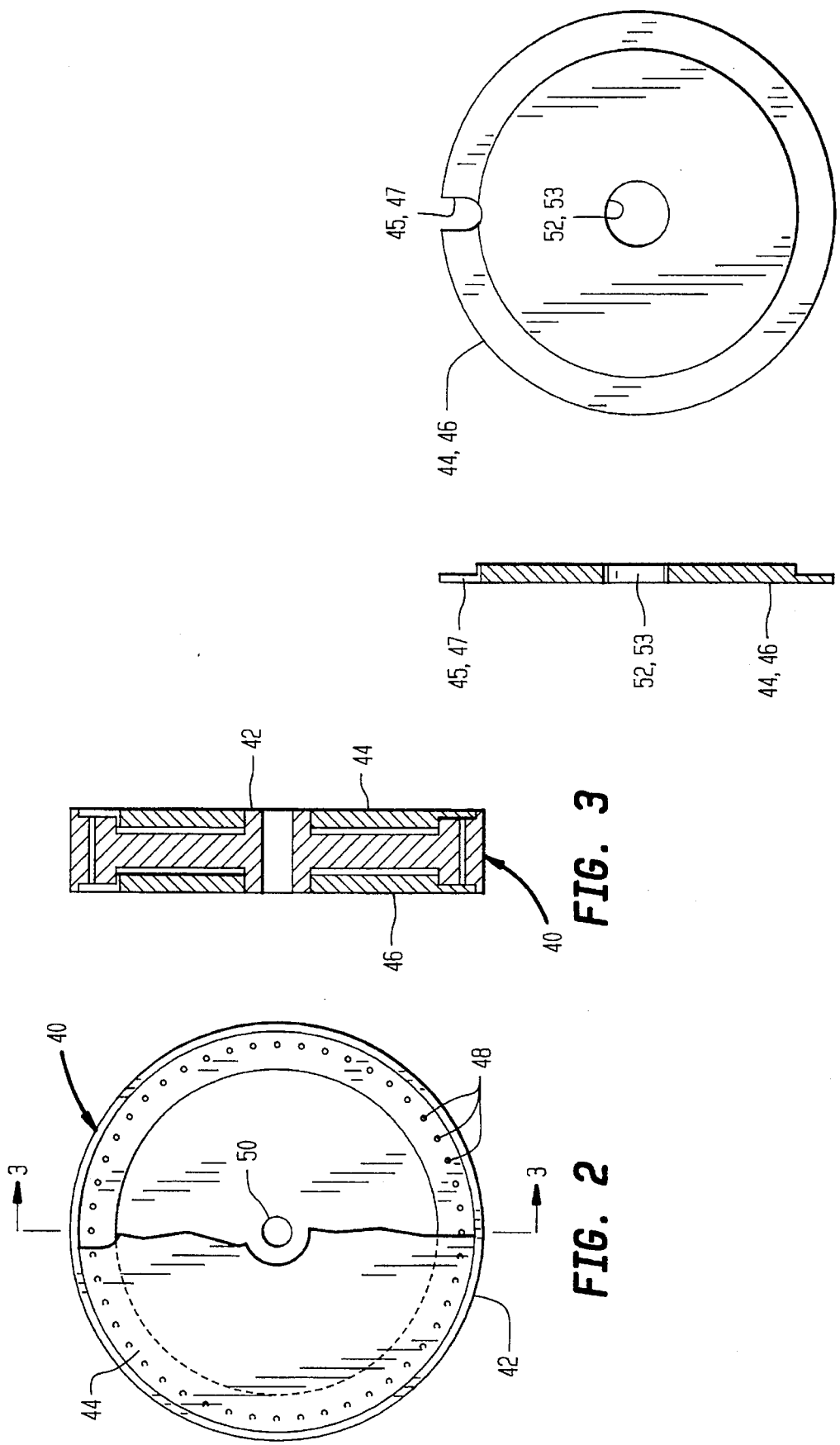

MICRO AND MINI HAIR TRANSPLANT DEVICE

BACKGROUND OF THE INVENTION

This invention generally relates to the field of plastic surgery. In particular, it relates to a device used to transplant hair into the scalp of a person suffering from baldness.

The available techniques for transplanting hair are time consuming and labor intensive. Generally, a surgeon and two technicians are required to perform the transplant procedure. The current technique begins by anesthetizing the patient locally in the place where the transplant will be performed. Hair is harvested in strips from the donor site referred to as the occipital scalp. The hair follicles are then taken by a technician and cut into hundreds of small hair grafts. In the meantime, the surgeon, assisted by a second technician, will use a scalpel and cut slits in the scalp where the hair is to be transplanted. Small metal rods, referred to as dilators, are placed in the holes in the scalp to keep them from closing until the hair grafts are placed therein.

There are two types of grafts. One is referred to as a minigraft and is made up of from 3 to 6 hair follicles. The second is referred to as a micrograft and is made up of only one hair follicle. Micrografts are used to form the frontal hairline while minigrafts are used over the rest of the thinning or balding scalp.

After placement of the dilator, each hair graft, either a micrograft or a minigraft, is placed in its respective slit manually and the dilator is removed. The scalp then closes around the transplanted hair graft.

A typical patient is subjected to many hundreds of these individual hair transplant grafts. Typically the average procedure lasts about 240 minutes. Given this time period, the patient normally requires a second dose of anesthesia to maintain proper comfort. This procedure suffers from the drawbacks of being time consuming, labor intensive and not being automated.

SUMMARY OF THE INVENTION

The present invention has the object of automating this procedure and thereby reducing the overall time required, increasing the comfort of the patient, and reducing manipulation of the grafts. The present invention is directed to a device that can be used to automate hair transplant procedures. In addition, the present invention is also directed to an automated hair transplant method. Both the device and the method of the present invention solve the problems inherent in the prior art procedures by reducing the amount of time needed to perform a hair transplant procedure and reducing to one, the number of technicians required to assist the surgeon.

The device of the present invention comprises a means for puncturing the scalp at the transplant site, a means for containing the hair grafts to be transplanted, a means for ejecting the hair grafts from the containing means, a means for actuating the ejecting means and a means for delivering the hair grafts into the transplant site. The method of the present invention comprises cutting the hair grafts to be transplanted, loading the hair grpfts into a plurality of devices for containing the hair, attaching one of the devices for containing the hair grafts onto a device of the present invention, ejecting the hair grafts from the device containing them into the scalp, removing the device containing the hair grafts, attaching a second device containing hair grafts and repeating the steps until all the hair grafts are transplanted.

BRIEF DESCRIPTION OF THE DRAWINGS

FIG. 2 is a plan view of a hair cylinder for use with the present invention.

FIG. 3 is a sectional side view of the hair cylinder of FIG. 2 taken along line 3—3 of FIG. 2.

FIG. 4 is a sectional side view of a cover plate for use with the hair cylinder of FIG. 2.

FIG. 5 is a plan view of the cover plate of FIG. 4.

DETAILED DESCRIPTION OF THE INVENTION

Figure 1:
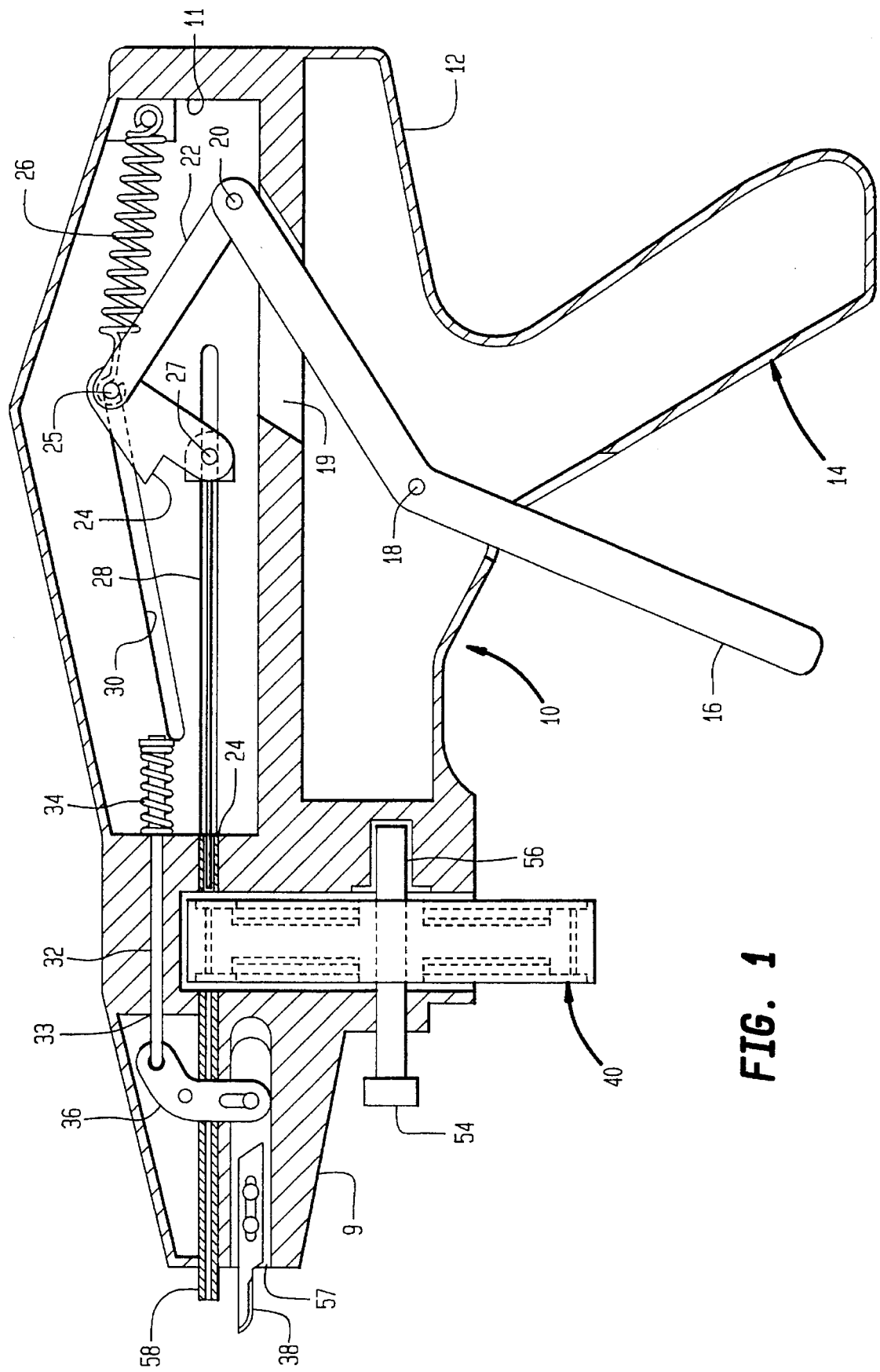
FIG. 1 is a cut away plan view of an embodiment of the present invention.

FIG. 1 illustrates one embodiment of an automated hair transplant device 10. Hair transplant device 10 comprises a partially hollow body 12 which encloses the moving parts of the device 10. The body 12 is generally in the shape of a gun and is meant to be held in the hand of the surgeon. Those of ordinary skill in the art will recognize that the shape of body 12 can be departed from without departing from the scope or spirit of the invention.

Handle 14 will rest in the palm of the surgeon's hand while the surgeon's fingers will wrap around actuating arm 16. Actuating arm 16 is mounted on two pivot pins 18 and 20. Pivot pin 18 is mounted on the interior of body 12. Actuating arm 16 can rotate about pivot pin 18 and be displaced laterally in slot 19. A connecting rod 22 is joined to actuating arm 16 at pivot pin 20. Connecting rod 22 is joined at its other end by a pivot pin 25 to an angled actuating arm 24 and to main spring 26. Main spring 26 is also mounted to the interior surface 11 of body 12. A hair push rod 28 is connected to the angled actuating arm 24 at a pivot pin 27. Hair push rod 28 fits slidably into cylindrical recess 29. Also connected to angled actuating arm 24, near the main spring 26, is a second connecting rod 30.

The second connecting rod 30 is connected on its opposite end to a knife push rod 32 and a second spring 34. The knife push rod 32 is connected at the other end to a knife actuating arm 36. Knife push rod 32 fits slidably into cylindrical recess 33. The other end of the knife actuating arm 36 is connected to a retractable scalpel blade 38.

The hair push rod 28 interacts with hair cylinder 40. Hair cylinder 40 is illustrated in detail in FIGS. 2 and 3. Hair cylinder 40 comprises cylinder core 42 and cover plates 44 and 46. Equally spaced around the circumference of cylinder core 42 are forty-eight equally spaced through holes 48. In this embodiment, holes 48 have an internal diameter of approximately 0.138 inch. During use, the hair grafts would be inserted into the holes 48. Cylinder core 42 also contains a larger through hole 50 of diameter 0.218 inch located at the center of the cylinder core 42. As illustrated is FIGS. 4 and 5, cover plates 44 and 46 also each contain a central through hole 52 and 53 respectively. In use, cylinder core 42 and cover plates 44 and 46 are fitted together to form hair cylinder 40. Cover plates 44 and 46 each contain a slot 45 and 47 respectively near their circumference so that the hair follicles can be ejected from cylinder core 42 during use.

Hair cylinder 40 is mounted to body 12 by means of a pin 54 as illustrated in FIG. 1. Pin 54 slides through holes 50, 52 and 53 and is fixed in a recess 56 in body 12. Cylinder core 42 is free to slidably rotate around pin 54 however, cylinder cover plates 44 and 46 are prevented from rotating by pin 54.

Figure 7:
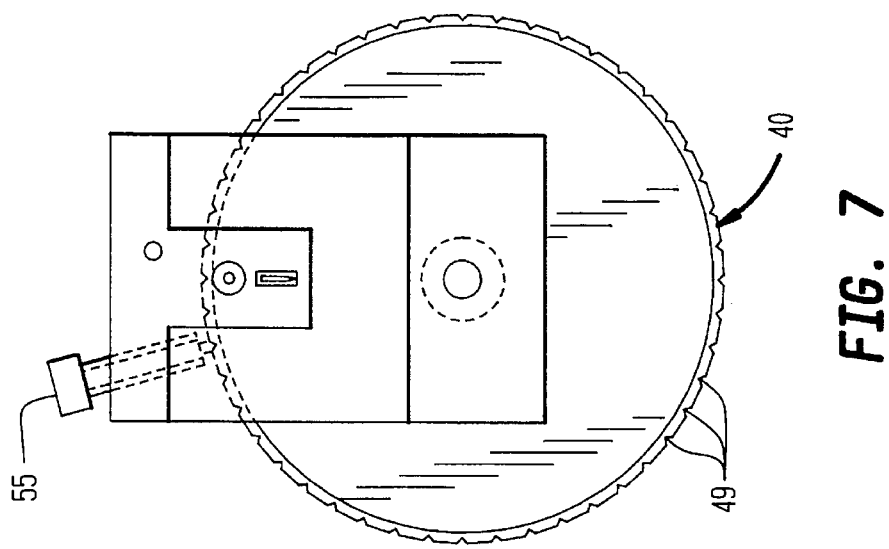
FIG. 7 is a plan view of the hair cylinder of FIG. 2 as mounted on the device of FIG. 1.

As illustrated in FIG. 7, the hair cylinder 40 has forty-eight indentations 49 located around its circumference. The indentations 49 are used to index the position of hair cylinder 40 by means of an indexing pin 55. The indexing pin 55 also serves to stabilize the cylinder cover plates 44 and 46 and prevent them from rotating.

The operating end 9 of transplant device 10 will now be described in further detail. Retractable scalpel blade 38 is axially aligned with and slidable in the axial direction in cylindrical shaped recess 57. A stationary hair barrel 58 is mounted just above scalpel blade 38. The hair barrel 58 is axially aligned with holes 45 and 47 in cover plates 44 and 46 which in turn are axially aligned with cylindrical recess 29 and hair push rod 28.

The method for using the hair transplant device 10 will now be described. First, the patient would be anesthetized with a local anesthetic in the area of the hair transplant. Then, the surgeon would begin by cutting hair strips from another area of the patient's scalp. A technician would take the hair strips and cut them into single hair minigrafts and multiple hair microgrpfts for transplanting. This embodiment of the present invention is intended to be used for transplanting minigrpfts. The minigrafts would then be placed individually into one of the holes 48 in cylinder core 42. Each hole 48 would contain only one minigraft. When each of the 48 holes 48 contains a minigraft, the technician will place cover plates 44 and 46 onto cylinder core 42. The assembled hair cylinder 40 will then be mounted onto body 12 by means of pivot pin 54.

As shown in FIG. 1, the retractable scalpel blade 38 is in its normal extended position. The surgeon will place end 9 of hair transplant device 10 onto the area of the scalp where the hair is to be transplanted and put a slit in the scalp with retractable scalpel blade 38. The surgeon will then squeeze actuating arm 16. The movement of actuating arm 16 will cause, through connecting rod 22, rotation of angled actuating arm 24 about point 25. Rotation of angled actuating arm 24 about point 25 will commence movement of the knife push rod 32 and the hair push rod 28. The knife push rod 32 will be actuated through movement of connecting rod 30. Knife push rod 32 will cause rotation of the knife actuating arm 36 about point 37. Rotation of the knife actuating arm 36 will cause the retractable scalpel blade 38 to retract into recess 57 due to the force provided by second spring 34.

Within less then 0.5 sec of the time of scalp puncture, hair push rod 28 will slide axially forward out of cylindrical recess 28, through hole 45 in cover plate 44, into one of the plurality of holes 48 and into contact with the hair graft to be transplanted. Hair push rod 48 will then push the hair graft through hole 47 in cover plate 46, into the hair barrel 58 and finally into the scalp puncture made by retractable scalpel blade 38. Hair push rod 28 will then quickly retract due to the force provided by main spring 26. Retractable scalpel blade 38 will then return to the extended position shown in FIG. 1.

Cylinder core 42 will then be rotated to bring the next hair graft into alignment with hair push rod 28. In this regard, cylinder core 42 is rotated until pin 55 is in contact with the next indentation 49. Although the embodiment herein described contemplates manual rotation of cylinder core 42, the present invention also contemplates automatic rotation of cylinder core 42 when actuating arm 16 is squeezed. After the hair cylinder is rotated, the procedure described above is repeated. The process of squeezing the actuating arm 16, transplanting the hair graft, and then rotating the cylinder core 42 is repeated until all the hair follicles in the hair cylinder 40 are implanted in the patient's scalp. At that point, another fully loaded hair cylinder 40 is placed into the hair transplant device 10 and the above described procedure is repeated. In the average hair transplant procedure, 7 to 10 fully loaded hair cylinders 40 would be used.

Figure 6:
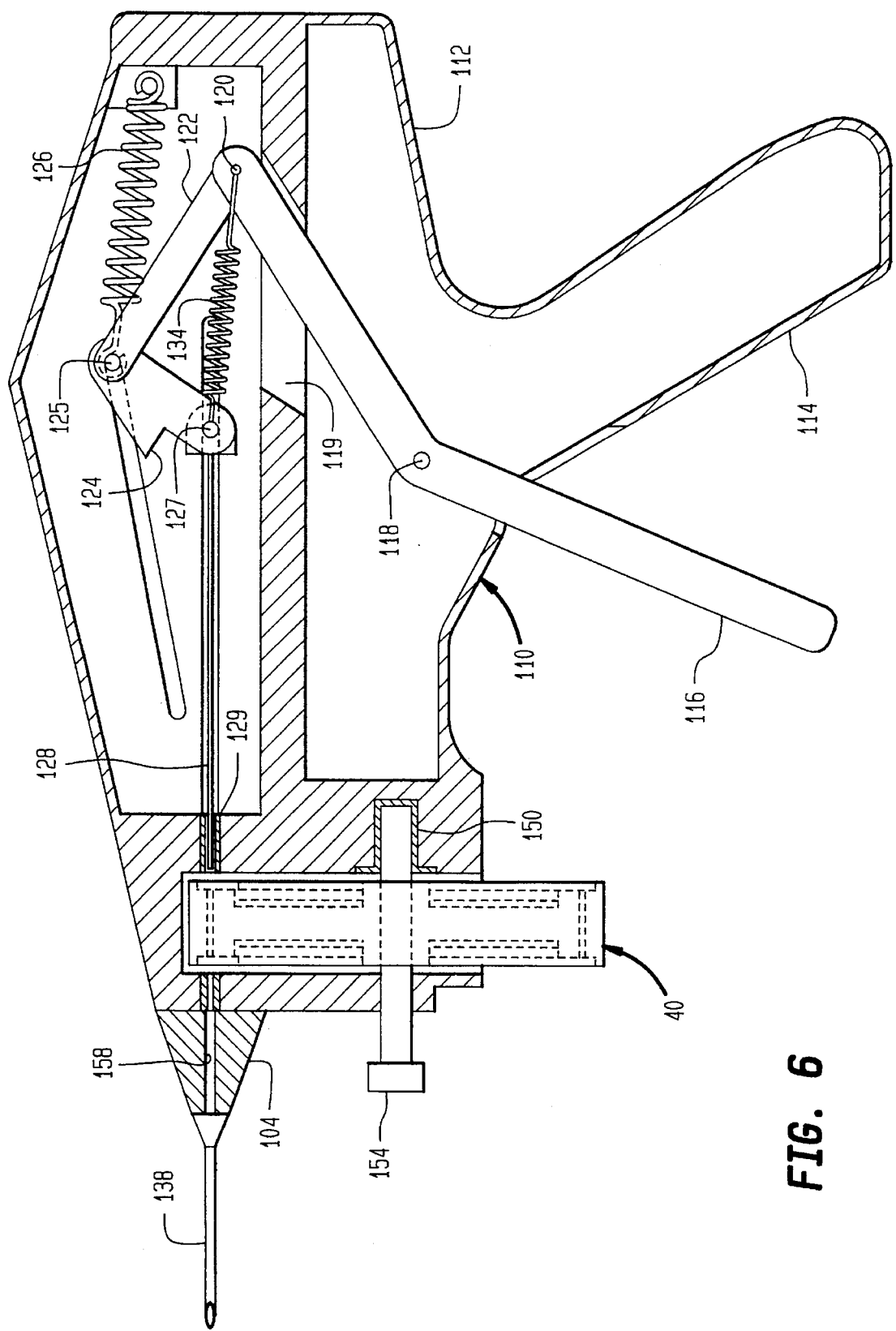
FIG. 6 is a cutaway plan view of a second embodiment of the present invention.

FIG. 6 illustrates an alternative embodiment 110 of the automated hair transplant device of the present invention. This particular embodiment is intended to be used for transplanting micrograms. Hair transplant device 110 comprises a partially hollow body 112 which encloses the moving parts of the device 110. The body 112 is generally in the shape of a gun and is meant to be held in the hand of the surgeon.

Handle 114 will rest in the palm of the surgeon's hand while the surgeon's fingers will wrap around actuating arm 116. Actuating arm 116 is mounted on two pivot pins 118 and 120. Pivot pin 118 is mounted on the interior of the body 112. Actuating arm 116 can rotate about pivot pin 118 and be laterally displaced in slot 119.

A connecting rod 122 is joined to actuating arm 116 at pivot pin 120. Also joined at pivot pin 120 with actuating arm 116 and connecting rod 122 is spring 134. Connecting rod 122 is joined at its other end by a pivot pin 125 to an angled actuating arm 124 and to main spring 126. Main spring 126 is also mounted to the interior surface of body 112. A hair push rod 128 is connected to the angled actuating arm 124 at pivot pin 127. Hair push rod 128 fits slidably into cylindrical recess 129.

Figure 9:
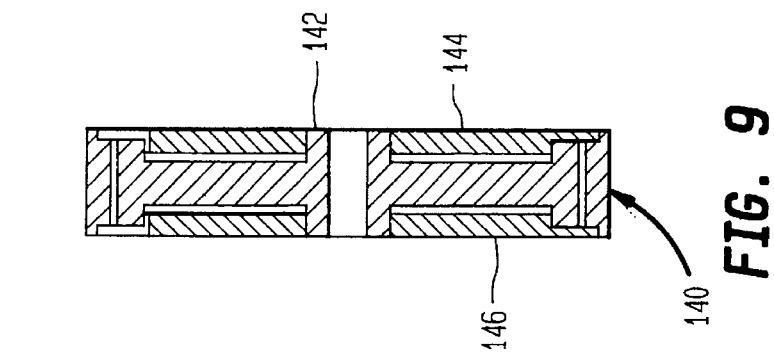
FIG. 9 is a sectional side view of the hair cylinder of FIG. 8 taken along line 9—9.
Figure 8:
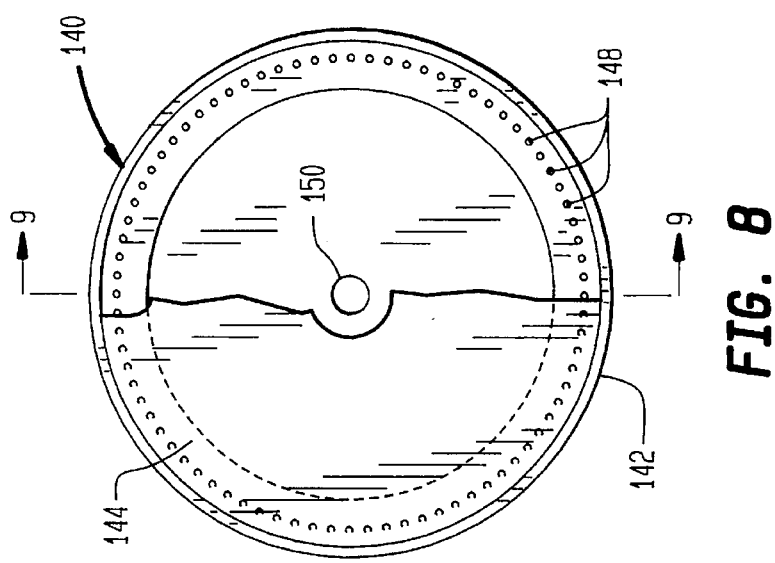
FIG. 8 is a plan view of a hair cylinder for use with the present invention.
Figure 11:
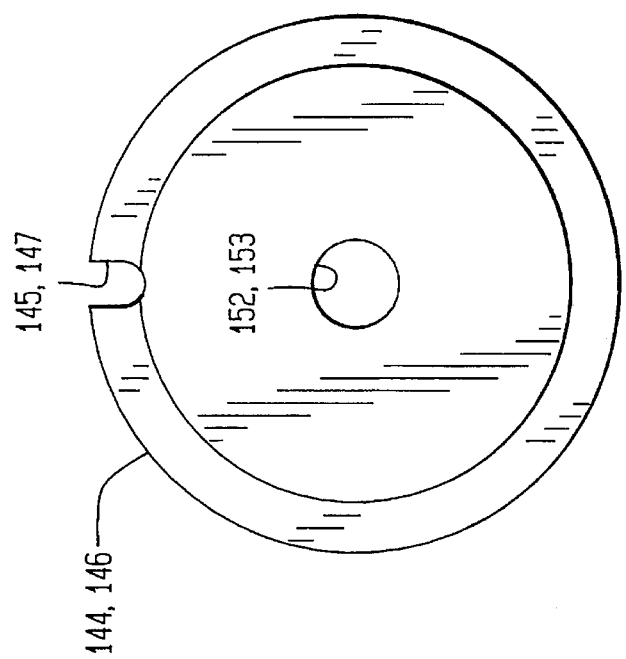
FIG. 11 is a plan view of the cover plate of FIG. 10.
Figure 10:
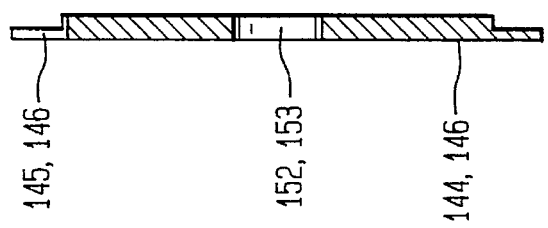
FIG. 10 is sectional side view of a cover plate for use with the hair cylinder of FIG. 8.

The hair push rod 128 interacts with a hair cylinder 140. As illustrated in FIGS. 8 and 9, hair cylinder 140 is similar to hair cylinder 40 of the previously described embodiment except for the internal diameter of the holes 148 carrying the hair grpfts. Hair cylinder 140 comprises cylinder core 142 and cover plates 144 and 146. Equally spaced around the circumference of cylinder 142 are eighty equally spaced holes 148. In this embodiment, holes 148 have an internal diameter of approximately 0.030 inch. This embodiment of the hair cylinder 140 is used in the same manner as the hair cylinder 40 of the prior embodiment with one microhair graff being placed in each of the eighty holes 148. Cylinder core 142 contains a through hole of diameter 0.218 inch located at the center of cylinder core 142. As illustrated in FIGS. 10 and 11, cover plates 144 and 146 also each contain a central through-hole 152 and 153 respectively. In use, cylinder core 142 and cover plates 144 and 146 are fitted together to form hair cylinder 140. Cover plates 144 and 146 each contain a slot 145 and 147 respectively near their circumference so that the hair follicles can be ejected from cylinder core 142 during use.

Hair cylinder 140 is mounted to body 112 by means of a pivot pin 154 as illustrated in FIG. 6. Pin 154 slides through holes 150 and 152 into a recess 156 in body 112. Cylinder core 142 is free to slidably rotate around pivot pin 154 while cover plates 144 and 146 are held in place by pivot pin 154.

Figure 12:
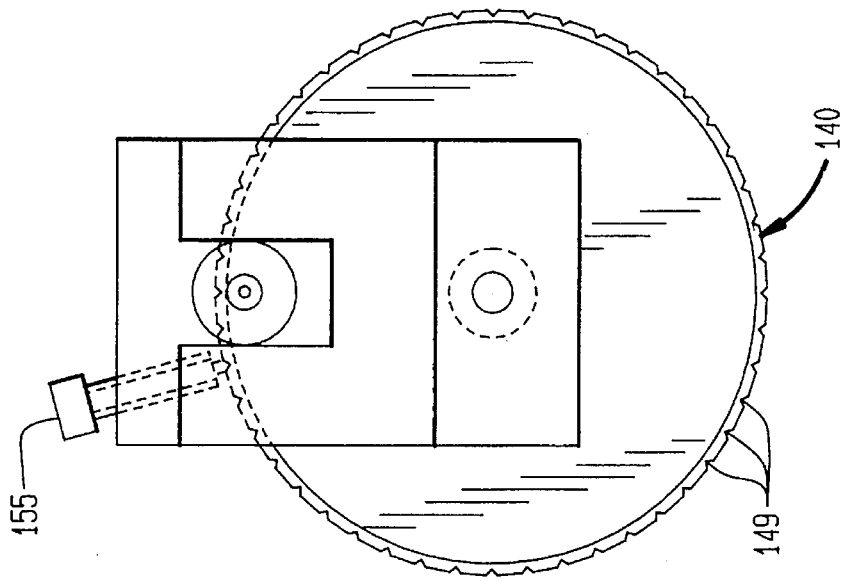
FIG. 12 is a plan view of the the hair cylinder of FIG. 8 as mounted on the device of FIG. 6.

As illustrated in FIG. 12, hair cylinder 140 has eighty indentations 149 located around its circumference. The indentations 149 are used to index the position of hair cylinder 140 by means of indexing pin 155. Indexing pin 155 also serves to stabilize cover plates 144 and 146 and prevent them from rotating.

The operating end 109 of hair transplant device 110 has a standard 18 gauge surgical needle 138 mounted thereon. The axis of needle 138 is aligned with the axis of a cylindrical recess 158 in body 112 which in turn is aligned with slots 145 and 147 in cover plates 144 and 146. Cylindrical recess 129 and hair push rod 128 are also axially aligned with slots 145 and 147.

The method for using this embodiment of the invention is identical to the method of using the prior embodiment with the following exceptions. The patient's scalp is punctured with the tip of needle 138 rather than by the scalpel blade 38. The internal mechanism for actuating the hair push rod 128 and ejecting the hair follicles is the same as in the prior embodiment. In this embodiment, hair push rod 128 ejects the microhair grafts from hair cylinder 40 directly through a lumen of needle 138 and into the puncture in the scalp.

Those of ordinary skill in the art will recognize that the embodiments just described merely illustrate the principles of the present invention. Many modifications may be made thereto without departing from the spirit and scope of the invention as set forth in the following claims.

What is claimed is:

1. A device for transplanting hair comprising:

a body member;

a first means for puncturing the scalp at a transplant site mounted to the body member comprising a retractable scalpel blade that is mounted in a first recess in the body member;

a second means for containing a plurality of hair grafts mounted in the body member such that the second means is free to rotate about an axis in the body member;

a third means, mounted slidably in a second recess in the body member and aligned with an axis of the body member, for ejecting the plurality of hair grafts from the second means by sliding along the axis of the body member through the second recess and into the second means;

a fourth means, connected to the body member and extending therefrom, and further connected to the third means, for actuating the third means and thereby ejecting hair hair grafts from the second means and further connected to the retractable scalpel blade to cause the retractable scalpel blade to retract into the first recess in the body member; and a fifth means, mounted in the body member and aligned with the axis of the body member, for delivering hair grafts from the second means into the transplant site.

2. The device of claim 1 wherein the second means comprises a rotatable cylinder containing a plurality of holes for receiving the plurality of hair grafts.

3. The device of claim 2 wherein the third means comprises a spring loaded push rod.

4. The device of claim 3 wherein the fifth means comprises a hollow plastic hair barrel.

* * * * *